(12) United States Patent
Duefel et al.

(10) Patent No.: US 10,197,559 B2
(45) Date of Patent: Feb. 5, 2019

(54) CHAPERONE-CHAPERONE FUSION POLYPEPTIDES FOR REDUCTION OF INTERFERENCE AND STABILIZATION OF IMMUNOASSAYS

(71) Applicant: Roche Diagnostics Operations, Inc., Indianapolis, IN (US)

(72) Inventors: Hartmut Duefel, Schlehdorf (DE); Alexander Riedel, Munich (DE); Peter Schaarschmidt, Ulm (DE); Urban Schmitt, Kochel (DE); Christian Scholz, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 52 days.

(21) Appl. No.: 14/640,263

(22) Filed: Mar. 6, 2015

(65) Prior Publication Data
US 2017/0261498 A1    Sep. 14, 2017

Related U.S. Application Data

(63) Continuation of application No. PCT/EP2013/068269, filed on Sep. 4, 2013.

(51) Int. Cl.
*C12N 9/90*      (2006.01)
*G01N 33/53*     (2006.01)
*C07K 14/245*    (2006.01)

(52) U.S. Cl.
CPC ....... *G01N 33/5306* (2013.01); *C07K 14/245* (2013.01); *C12N 9/90* (2013.01); *C12Y 502/01008* (2013.01); *C07K 2319/35* (2013.01); *C07K 2319/735* (2013.01)

(58) Field of Classification Search
None
See application file for complete search history.

(56) References Cited

FOREIGN PATENT DOCUMENTS

| EP | 1982993 A2 | 10/2008 | |
|---|---|---|---|
| EP | 2127 679 A1 * | 2/2009 | ............ A61K 47/48 |
| EP | 2127678 A1 | 12/2009 | |
| EP | 2127679 A1 | 12/2009 | |
| WO | 2003/000878 A2 | 1/2003 | |
| WO | 2007/077008 A1 | 7/2007 | |
| WO | WO 2007/077008 A1 * | 7/2007 | ............ C12N 9/90 |
| WO | 2009/074318 A2 | 6/2009 | |

OTHER PUBLICATIONS

Hong, So Yeon et al., Soluble Expression of Candida antarctica Lipase B in *Escherichia coli* by Fusion with Skp Chaperone, Biotechnology and Bioprocess Engineering, 2012, pp. 687-682, vol. 17.
International Search Report dated Dec. 2, 2013, in Application No. PCT/EP2013/068269, 5 pages.
Knappe, Thomas A. et al., "Insertion of a Chaperone Domain Converts FKBP12 into a Powerful Catalyst of Protein Folding," Journal of Molecular Biology, 2007, pp. 1458-1468, vol. 368.
Quistgaard, Esben M. et al., "High-resolution insights into binding of unfolded polypeptides by the PPIase chaperone SlpA," The FASEB Journal, 2012, pp. 4003-4013, vol. 26.
Scholz, Christian et al., "Functional Solubilization of Aggregation-prone HIV Envelope Proteins by Covalent Fusion with Chaperone Modules," Journal of Molecular Biology, 2005, pp. 1229-1241, vol. 345.
Scholz, Christian et al., "SlyD Proteins from Different Species Exhibit High Prolyl Isomerase and Chaperone Activities," Biochemistry, 2006, pp. 20-33, vol. 45.

* cited by examiner

*Primary Examiner* — Lisa V Cook
(74) *Attorney, Agent, or Firm* — Stinson Leonard Street LLP

(57) ABSTRACT

The invention concerns a fusion polypeptide including several molecules of folding helper polypeptides, including one multimerization domain, in particular Skp, and at least one molecule of SlyD or SlpA, wherein no further target polypeptide sequences are fused to the fusion polypeptide. The invention further concerns an immunoassay and the use of the fusion polypeptide in an immunoassay for reduction of interferences or minimizing false positive results or for stabilizing proteinaceous assay reagents. Further the invention concerns a reagent kit for use in an immunoassay comprising the fusion polypeptide.

6 Claims, 11 Drawing Sheets
Specification includes a Sequence Listing.

FIG. 1

| Run | V1 | V2 | |
|---|---|---|---|
| R1 | FF41-Bi | FF41-Bi | |
| SS-Helix (GDA,P) in R1 | without anti-interference additive | 25µg/ml | |
| R2 | SS41-Ru | SS41-Ru | |
| Average negative sera | 2,163 | 1,605 | |
| sample | counts | counts | Δ signal |
| Trina 10/2008-244 | 1,705 | 1,598 | 107 |
| Trina 10/2008-245 | 1,581 | 1,540 | 41 |
| Trina 10/2008-246 | 1,767 | 1,563 | 204 |
| Trina 10/2008-247 | 1,636 | 1,626 | 10 |
| Trina 10/2008-248 | 3,541 | 1,678 | 1,863 |
| Trina 10/2008-249 | 1,615 | 1,612 | 3 |
| Trina 10/2008-250 | 1,644 | 1,580 | 64 |
| Trina 10/2008-251 | 1,593 | 1,577 | 16 |
| Trina 10/2008-252 | 1,581 | 1,613 | 32 |
| Trina 10/2008-253 | 1,594 | 1,609 | 15 |
| Trina 10/2008-254 | 1,573 | 1,603 | 30 |
| Trina 10/2008-255 | 8,195 | 1,596 | 6,599 |
| Trina 10/2008-257 | 2,295 | 1,885 | 410 |
| Trina 10/2008-258 | 1,686 | 1,699 | 13 |
| Trina 10/2008-259 | 1,621 | 1,585 | 36 |
| Trina 10/2008-261 | 2,155 | 1,593 | 562 |

FIG. 2

| Run | V1 | V2 | |
|---|---|---|---|
| R1 | FF41-Bi | FF41-Bi | |
| SS-Helix (GDA,P) in R1 | without anti-interference additive | 25µg/ml | |
| R2 | SS41-Ru | SS41-Ru | |
| Average negative sera | 2,163 | 1,605 | |
| sample | counts | counts | Δ signal |
| Trina 10/2008-262 | 1,763 | 1,740 | 23 |
| Trina 10/2008-264 | 1,685 | 1,631 | 54 |
| Trina 10/2008-265 | 1,605 | 1,529 | 76 |
| Trina 10/2008-266 | 1,837 | 1,505 | 332 |
| Trina 10/2008-268 | 4,608 | 1,846 | 2,762 |
| Trina 10/2008-269 | 1,646 | 1,637 | 9 |
| Trina 10/2008-270 | 1,609 | 1,562 | 47 |
| Trina 10/2008-272 | 1,883 | 1,496 | 387 |
| Trina 10/2008-273 | 1,858 | 1,551 | 307 |
| Trina 10/2008-274 | 1,611 | 1,578 | 33 |
| Trina 10/2008-275 | 1,581 | 1,560 | 21 |
| Trina 10/2008-276 | 1,848 | 1,582 | 266 |
| Trina 10/2008-277 | 3,969 | 1,438 | 2,531 |
| Trina 10/2008-279 | 1,609 | 1,546 | 63 |

FIG. 3

| Run | V1 | V2 | |
|---|---|---|---|
| R1 | FF41-Bi | FF41-Bi | |
| SS-Helix (GDA,P) in R1 | without anti-interference additive | 25µg/ml | |
| R2 | SS41-Ru | SS41-Ru | |
| Average negative sera | 2,163 | 1,605 | |
| Sample | counts | counts | Δ signal |
| Trina 10/2008 16097448 | 46,498 | 1,549 | 44,949 |
| Trina 10/2008-752 | 42,475 | 1,603 | 40,872 |
| Trina 10/2008-430 | 36,659 | 1,527 | 35,132 |
| Trina 10/2008-34103923 | 15,098 | 1,495 | 13,603 |
| Trina 10/2008-34045926 | 20,015 | 1,558 | 18,457 |
| Trina 10/2008-16097705 | 50,728 | 2,489 | 48,239 |
| HIV-1 B ESS | 136,466 | 136,475 | 9 |
| HIV-1 C ESS | 24,933 | 25,071 | 138 |

FIG. 4

| | V0 | V1 | | V2 | | V3 | |
|---|---|---|---|---|---|---|---|
| | without anti-interference additive | EcSlyD-EcSlyD-Helix (GDA,P) chem. SlyD polymer | | EcSkp-EcSlyD | | EcSkp-EcSlyD-EcSlyD rec. SlyD polymer | |
| Lot no. | - | 14818100 | | DA120711 | | DA191211 | |
| conc. [µg/ml] | - | 5 | 25 | 5 | 25 | 5 | 25 |
| sample | counts | counts | counts | counts | counts | counts | counts |
| HIV neg. | 553 | 505 | 516 | 542 | 532 | 667 | 536 |
| HIV neg. | 534 | 511 | 532 | 527 | 522 | 670 | 518 |
| HIV neg. | 697 | 503 | 516 | 611 | 548 | 508 | 528 |
| HIV neg. | 764 | 512 | 519 | 697 | 635 | 523 | 515 |
| HIV neg. | 835 | 837 | 859 | 829 | 829 | 977 | 827 |
| HIV 1 A | 107,331 | 95,768 | 97,576 | 104,272 | 102,956 | 95,377 | 101,216 |
| HIV 1 B | 181,576 | 167,163 | 166,689 | 177,264 | 181,656 | 169,119 | 178,083 |
| HIV 1 C | 59,673 | 58,768 | 58,579 | 60,088 | 62,915 | 59,694 | 62,148 |
| HIV 1 E | 94,352 | 92,411 | 94,825 | 94,634 | 99,620 | 94,221 | 98,174 |
| HIV 1 F | 95,476 | 89,220 | 90,910 | 92,884 | 97,817 | 90,099 | 97,244 |
| Trina 16097448 | 59,827 | 1,971 | 548 | 28,729 | 10,594 | 1,676 | 621 |
| Trina 47101943 | 53,491 | 1,915 | 647 | 26,812 | 9,960 | 1,700 | 732 |

FIG. 5

|  | V0 | V4 | | V5 | |
|---|---|---|---|---|---|
|  | without anti-interference additive | EcSlyD | | EcSkp | |
| Lot no. | - | DA240210 | | DA240210 | |
| conc. [µg/ml] | - | 5 | 25 | 5 | 25 |
| Sample | counts | counts | counts | counts | counts |
| HIV neg. | 553 | 548 | 632 | 533 | 654 |
| HIV neg. | 534 | 520 | 517 | 673 | 494 |
| HIV neg. | 697 | 707 | 695 | 668 | 673 |
| HIV neg. | 764 | 745 | 745 | 748 | 724 |
| HIV neg. | 835 | 954 | 837 | 779 | 727 |
| HIV 1 A | 107,331 | 105,073 | 108,133 | 105,907 | 98,209 |
| HIV 1 B | 181,576 | 172,663 | 178,522 | 184,720 | 179,742 |
| HIV 1 C | 59,673 | 58,856 | 59,836 | 62,420 | 65,924 |
| HIV 1 E | 94,352 | 92,870 | 94,295 | 98,564 | 97,617 |
| HIV 1 F | 95,476 | 93,059 | 94,117 | 100,071 | 102,886 |
| Trina 16097448 | 59,827 | 57,754 | 59,184 | 60,332 | 58,333 |
| Trina 47101943 | 53,491 | 52,086 | 52,559 | 53,131 | 52,081 |

FIG. 6

| | V0 | V6 | V7 | | V8 | |
|---|---|---|---|---|---|---|
| | without anti-interference additive | EcSlyD-EcSlyD-EcSlyD-EcSlyD-EcSlyD | EcSlyD-EcSlyD-EcSlyD | | EcSlyD-EcSlyD | |
| Lot no. | - | LT050204 | LT090511 | | DA170112 | |
| conc. [µg/ml] | - | 5 | 5 | 25 | 5 | 25 |
| Sample | counts | counts | counts | counts | counts | counts |
| HIV neg. | 553 | 541 | 539 | 546 | 558 | 621 |
| HIV neg. | 534 | 518 | 521 | 538 | 527 | 552 |
| HIV neg. | 697 | 539 | 662 | 582 | 690 | 690 |
| HIV neg. | 764 | 574 | 711 | 619 | 829 | 819 |
| HIV neg. | 835 | 885 | 860 | 844 | 884 | 837 |
| HIV 1 A | 107,331 | 96,510 | 103,838 | 99,776 | 106,706 | 106,344 |
| HIV 1 B | 181,576 | 169,248 | 175,285 | 172,557 | 177,242 | 177,123 |
| HIV 1 C | 59,673 | 59,550 | 59,874 | 59,306 | 59,398 | 59,301 |
| HIV 1 E | 94,352 | 93,694 | 94,641 | 95,656 | 93,600 | 93,815 |
| HIV 1 F | 95,476 | 91,795 | 94,816 | 91,521 | 94,559 | 94,463 |
| Trina 16097448 | 59,827 | 1,660 | 21,260 | 4,208 | 57,174 | 55,254 |
| Trina 47101943 | 53,491 | 1,679 | 19,084 | 3,858 | 51,039 | 50,833 |

FIG. 7

| | | V0 | V1 | V2 | |
|---|---|---|---|---|---|
| | | without anti-interference additive | rec. EcSlyD-EcSlyD-Helix (GDA,P) | EcSkp-EcSlyD-EcSlyD | |
| | Lot no. | | 30117200 | DA140711 | |
| conc. [µg/ml] | | --- | 20 | 5 | 15 |
| sample | | counts | counts | counts | counts |
| HIV neg. | Pr163 | 522 | 526 | 503 | 515 |
| HIV neg. | Pr4 | 526 | 517 | 498 | 507 |
| HIV neg. | Pr104 | 524 | 512 | 495 | 514 |
| HIV neg. | C131652 | 505 | 501 | 486 | 502 |
| HIV neg. | C131800 | 535 | 522 | 508 | 514 |
| HIV 1 pos. | 0060.0003.01 | 117,744 | 121,433 | 131,903 | 122,261 |
| HIV 1 pos. | 0060.0004.01 | 125,053 | 127,248 | 138,328 | 127,029 |
| HIV 1 pos. | 0060.0005.01 | 18,510 | 18,879 | 20,294 | 18,751 |
| HIV 1 pos. | 0060.0006.01 | 11,473 | 11,861 | 12,818 | 11,794 |
| HIV 1 pos. | 0060.0007.01 | 49,192 | 51,083 | 55,537 | 50,815 |
| Interf. | C133202 | 10,351 | 8,042 | 739 | 566 |
| Interf. | Pr149 | 1,437 | 903 | 536 | 537 |
| Interf. | C133111 | 778 | 772 | 486 | 507 |

FIG. 10

| Device | e411#837-10 | e411#837-10 | e411#837-10 | e411#837-10 | e411#837-10 |
|---|---|---|---|---|---|
| Run | V1 | V2 | V3 | V4 | V5 |
| R1 | PmSlyD-mgG2-Bi | PmSlyD-mgG2-Bi | PmSlyD-mgG2-Bi | PmSlyD-mgG2-Bi | PmSlyD-mgG2-Bi |
| Anti-interference additive in R1 | without anti-interference additive | EcSlpA-EcSlpA (GDA,P) 10 µg/ml | EcSkp-EcSlpA-EcSlpA 10 µg/ml | EcSkp 10µg/ml | EcSlpA 10 µg/ml |
| R2 | EcSlpA-mgG2-Ru | EcSlpA-mgG2-Ru | EcSlpA-mgG2-Ru | EcSlpA-mgG2-Ru | EcSlpA-mgG2-Ru |
| Anti-interference additive in R2 | without anti-interference additive | EcSlpA-EcSlpA (GDA,P) 10 µg/ml | EcSkp-EcSlpA-EcSlpA 10 µg/ml | EcSkp 10µg/ml | EcSlpA 10 µg/ml |
|  | counts | counts | counts | counts | counts |
| anti-HSV-2 negative sera |  |  |  |  |  |
| sample001 | 1,534 | 1,298 | 1,280 | 1,539 | 1,544 |
| sample002 | 1,270 | 1,155 | 1,136 | 1,286 | 1,254 |
| sample003 | 617 | 616 | 607 | 629 | 597 |
| sample004 | 709 | 700 | 688 | 712 | 728 |
| anti-HSV-2 positive sera |  |  |  |  |  |
| sample005 | 60,247 | 60,039 | 60,339 | 59,739 | 59,797 |
| sample006 | 16,013 | 15,811 | 15,870 | 15,739 | 15,559 |
| sample007 | 34,176 | 33,570 | 33,605 | 33,762 | 33,729 |
| sample008 | 207,083 | 207,167 | 207,902 | 206,063 | 206,774 |
| Sample009 | 11,365 | 11,345 | 11,072 | 11,218 | 11,367 |
| interference sera |  |  |  |  |  |
| sample010 | 15,889 | 5,790 | 4,763 | 16,288 | 12,953 |
| sample011 | 8,204 | 2,870 | 1,021 | 6,222 | 969 |
| sample012 | 42,168 | 864 | 856 | 38,631 | 14,801 |
| sample013 | 19,667 | 1,348 | 896 | 19,595 | 21,361 |

SEQUENCE LISTING

```
<160> NUMBER OF SEQ ID NOS: 9

<210> SEQ ID NO 1
<211> LENGTH: 529
<212> TYPE: PRT
<213> ORGANISM: Artificial Sequence
<220> FEATURE:
<223> OTHER INFORMATION: Synthetic

<400> SEQUENCE: 1

Ala Asp Lys Ile Ala Ile Val Asn Met Gly Ser Leu Phe Gln Gln Val
1               5                   10                  15

Ala Gln Lys Thr Gly Val Ser Asn Thr Leu Glu Asn Glu Phe Arg Gly
            20                  25                  30

Arg Ala Ser Glu Leu Gln Arg Met Glu Thr Asp Leu Gln Ala Lys Met
        35                  40                  45

Lys Lys Leu Gln Ser Met Lys Ala Gly Ser Asp Arg Thr Lys Leu Glu
    50                  55                  60

Lys Asp Val Met Ala Gln Arg Gln Thr Phe Ala Gln Lys Ala Gln Ala
65                  70                  75                  80

Phe Glu Gln Asp Arg Ala Arg Arg Ser Asn Glu Glu Arg Gly Lys Leu
                85                  90                  95

Val Thr Arg Ile Gln Thr Ala Val Lys Ser Val Ala Asn Ser Gln Asp
            100                 105                 110

Ile Asp Leu Val Val Asp Ala Asn Ala Val Ala Tyr Asn Ser Ser Asp
        115                 120                 125

Val Lys Asp Ile Thr Ala Asp Val Leu Lys Gln Val Lys Gly Gly Gly
    130                 135                 140
```

```
Ser Gly Gly Gly Ser Gly Gly Ser Gly Gly Ser Gly Gly Gly
    145                 150                 155                 160
Ser Gly Gly Gly Met Lys Val Ala Lys Asp Leu Val Val Ser Leu Ala
                165                 170                 175
Tyr Gln Val Arg Thr Glu Asp Gly Val Leu Val Asp Glu Ser Pro Val
                180                 185                 190
Ser Ala Pro Leu Asp Tyr Leu His Gly His Gly Ser Leu Ile Ser Gly
            195                 200                 205
Leu Glu Thr Ala Leu Glu Gly His Glu Val Gly Asp Lys Phe Asp Val
        210                 215                 220
Ala Val Gly Ala Asn Asp Ala Tyr Gly Gln Tyr Asp Glu Asn Leu Val
225                 230                 235                 240
Gln Arg Val Pro Lys Asp Val Phe Met Gly Val Asp Glu Leu Gln Val
                245                 250                 255
Gly Met Arg Phe Leu Ala Glu Thr Asp Gln Gly Pro Val Pro Val Glu
                260                 265                 270
Ile Thr Ala Val Glu Asp His Val Val Asp Gly Asn His Met
                275                 280                 285
Leu Ala Gly Gln Asn Leu Lys Phe Asn Val Glu Val Ala Ile Arg
        290                 295                 300
Glu Ala Thr Glu Glu Leu Ala His Gly His Val His Gly Ala His
305                 310                 315                 320
Asp His His His Asp His Asp Gly Gly Ser Gly Gly Gly
                325                 330                 335
Ser Gly Gly Gly Ser Gly Gly Ser Gly Gly Gly Ser Gly Gly Gly
            340                 345                 350
Met Lys Val Ala Lys Asp Leu Val Val Ser Leu Ala Tyr Gln Val Arg
                355                 360                 365
Thr Glu Asp Gly Val Leu Val Asp Glu Ser Pro Val Ser Ala Pro Leu
        370                 375                 380
Asp Tyr Leu His Gly His Gly Ser Leu Ile Ser Gly Leu Glu Thr Ala
385                 390                 395                 400
Leu Glu Gly His Glu Val Gly Asp Lys Phe Asp Val Ala Val Gly Ala
                405                 410                 415
Asn Asp Ala Tyr Gly Gln Tyr Asp Glu Asn Leu Val Gln Arg Val Pro
                420                 425                 430
Lys Asp Val Phe Met Gly Val Asp Glu Leu Gln Val Gly Met Arg Phe
            435                 440                 445
Leu Ala Glu Thr Asp Gln Gly Pro Val Pro Val Glu Ile Thr Ala Val
        450                 455                 460
Glu Asp His Val Val Asp Gly Asn His Met Leu Ala Gly Gln
465                 470                 475                 480
Asn Leu Lys Phe Asn Val Glu Val Val Ala Ile Arg Glu Ala Thr Glu
                485                 490                 495
Glu Glu Leu Ala His Gly His Val His Gly Ala His Asp His His
            500                 505                 510
Asp His Asp His Asp Gly Gly Gly Ser His His His His His His
        515                 520                 525
His

<210> SEQ ID NO 2
<211> LENGTH: 161
<212> TYPE: PRT
<213> ORGANISM: Escherichia coli
```

-continued

<400> SEQUENCE: 2

Met Lys Lys Trp Leu Leu Ala Ala Gly Leu Gly Leu Ala Leu Ala Thr
1               5                   10                  15

Ser Ala Gln Ala Ala Asp Lys Ile Ala Ile Val Asn Met Gly Ser Leu
            20                  25                  30

Phe Gln Gln Val Ala Gln Lys Thr Gly Val Ser Asn Thr Leu Glu Asn
        35                  40                  45

Glu Phe Lys Gly Arg Ala Ser Glu Leu Gln Arg Met Glu Thr Asp Leu
    50                  55                  60

Gln Ala Lys Met Lys Lys Leu Gln Ser Met Lys Ala Gly Ser Asp Arg
65                  70                  75                  80

Thr Lys Leu Glu Lys Asp Val Met Ala Gln Arg Gln Thr Phe Ala Gln
                85                  90                  95

Lys Ala Gln Ala Phe Glu Gln Asp Arg Ala Arg Arg Ser Asn Glu Glu
            100                 105                 110

Arg Gly Lys Leu Val Thr Arg Ile Gln Thr Ala Val Lys Ser Val Ala
        115                 120                 125

Asn Ser Gln Asp Ile Asp Leu Val Val Asp Ala Asn Ala Val Ala Tyr
    130                 135                 140

Asn Ser Ser Asp Val Lys Asp Ile Thr Ala Asp Val Leu Lys Gln Val
145                 150                 155                 160

Lys

<210> SEQ ID NO 3
<211> LENGTH: 196
<212> TYPE: PRT
<213> ORGANISM: Escherichia coli

<400> SEQUENCE: 3

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Cys Cys Gly Gly His Gly His Asp His Gly
                165                 170                 175

His Glu His Gly Gly Glu Gly Cys Cys Gly Gly Lys Gly Asn Gly Gly
            180                 185                 190

```
Cys Gly Cys His
        195

<210> SEQ ID NO 4
<211> LENGTH: 23
<212> TYPE: PRT
<213> ORGANISM: Artificial Sequence
<220> FEATURE:
<223> OTHER INFORMATION: Synthetic

<400> SEQUENCE: 4

Gly Gly Gly Ser Gly Gly Gly Ser Gly Gly Ser Gly Gly Gly Ser
1               5                   10                  15

Gly Gly Gly Ser Gly Gly Gly
            20

<210> SEQ ID NO 5
<211> LENGTH: 12
<212> TYPE: PRT
<213> ORGANISM: Artificial Sequence
<220> FEATURE:
<223> OTHER INFORMATION: Synthetic

<400> SEQUENCE: 5

Gly Gly Gly Ser His His His His His His His
1               5                   10

<210> SEQ ID NO 6
<211> LENGTH: 270
<212> TYPE: PRT
<213> ORGANISM: Escherichia coli

<400> SEQUENCE: 6

Met Lys Ser Leu Phe Lys Val Thr Leu Leu Ala Thr Thr Met Ala Val
1               5                   10                  15

Ala Leu His Ala Pro Ile Thr Phe Ala Ala Glu Ala Ala Lys Pro Ala
            20                  25                  30

Thr Ala Ala Asp Ser Lys Ala Ala Phe Lys Asn Asp Asp Gln Lys Ser
        35                  40                  45

Ala Tyr Ala Leu Gly Ala Ser Leu Gly Arg Tyr Met Glu Asn Ser Leu
    50                  55                  60

Lys Glu Gln Glu Lys Leu Gly Ile Lys Leu Asp Lys Asp Gln Leu Ile
65                  70                  75                  80

Ala Gly Val Gln Asp Ala Phe Ala Asp Lys Ser Lys Leu Ser Asp Gln
                85                  90                  95

Glu Ile Glu Gln Thr Leu Gln Ala Phe Glu Ala Arg Val Lys Ser Ser
            100                 105                 110

Ala Gln Ala Lys Met Glu Lys Asp Ala Ala Asp Asn Glu Ala Lys Gly
        115                 120                 125

Lys Glu Tyr Arg Glu Lys Phe Ala Lys Glu Lys Gly Val Lys Thr Ser
    130                 135                 140

Ser Thr Gly Leu Val Tyr Gln Val Val Glu Ala Gly Lys Gly Glu Ala
145                 150                 155                 160

Pro Lys Asp Ser Asp Thr Val Val Val Asn Tyr Lys Gly Thr Leu Ile
                165                 170                 175

Asp Gly Lys Glu Phe Asp Asn Ser Tyr Thr Arg Gly Glu Pro Leu Ser
            180                 185                 190

Phe Arg Leu Asp Gly Val Ile Pro Gly Trp Thr Glu Gly Leu Lys Asn
        195                 200                 205
```

Ile Lys Lys Gly Gly Lys Ile Lys Leu Val Ile Pro Pro Glu Leu Ala
    210                 215                 220

Tyr Gly Lys Ala Gly Val Pro Gly Ile Pro Pro Asn Ser Thr Leu Val
225                 230                 235                 240

Phe Asp Val Glu Leu Leu Asp Val Lys Pro Ala Pro Lys Ala Asp Ala
                245                 250                 255

Lys Pro Glu Ala Asp Ala Lys Ala Ala Asp Ser Ala Lys Lys
        260                 265                 270

<210> SEQ ID NO 7
<211> LENGTH: 149
<212> TYPE: PRT
<213> ORGANISM: Escherichia coli

<400> SEQUENCE: 7

Met Ser Glu Ser Val Gln Ser Asn Ser Ala Val Leu Val His Phe Thr
1               5                   10                  15

Leu Lys Leu Asp Asp Gly Thr Thr Ala Glu Ser Thr Arg Asn Asn Gly
            20                  25                  30

Lys Pro Ala Leu Phe Arg Leu Gly Asp Ala Ser Leu Ser Glu Gly Leu
        35                  40                  45

Glu Gln His Leu Leu Gly Leu Lys Val Gly Asp Lys Thr Thr Phe Ser
    50                  55                  60

Leu Glu Pro Asp Ala Ala Phe Gly Val Pro Ser Pro Asp Leu Ile Gln
65                  70                  75                  80

Tyr Phe Ser Arg Arg Glu Phe Met Asp Ala Gly Glu Pro Glu Ile Gly
                85                  90                  95

Ala Ile Met Leu Phe Thr Ala Met Asp Gly Ser Glu Met Pro Gly Val
            100                 105                 110

Ile Arg Glu Ile Asn Gly Asp Ser Ile Thr Val Asp Phe Asn His Pro
        115                 120                 125

Leu Ala Gly Gln Thr Val His Phe Asp Ile Glu Val Leu Glu Ile Asp
    130                 135                 140

Pro Ala Leu Glu Ala
145

<210> SEQ ID NO 8
<211> LENGTH: 199
<212> TYPE: PRT
<213> ORGANISM: Pasteurella multocida

<400> SEQUENCE: 8

Met Lys Ile Ala Lys Asn Val Val Ser Ile Ala Tyr Gln Val Arg
1               5                   10                  15

Thr Glu Asp Gly Val Leu Val Asp Glu Ala Pro Val Asn Gln Pro Leu
            20                  25                  30

Glu Tyr Leu Gln Gly His Asn Asn Leu Val Ile Gly Leu Glu Asn Ala
        35                  40                  45

Leu Glu Gly Lys Ala Val Gly Asp Lys Phe Glu Val Arg Val Lys Pro
    50                  55                  60

Glu Glu Ala Tyr Gly Glu Tyr Asn Glu Asn Met Val Gln Arg Val Pro
65                  70                  75                  80

Lys Asp Val Phe Gln Gly Val Asp Glu Leu Val Val Gly Met Arg Phe
                85                  90                  95

Ile Ala Asp Thr Asp Ile Gly Pro Leu Pro Val Val Ile Thr Glu Val
            100                 105                 110

Ala Glu Asn Asp Val Val Asp Gly Asn His Met Leu Ala Gly Gln
            115                 120                 125

Glu Leu Leu Phe Ser Val Glu Val Ala Thr Arg Glu Ala Thr Leu
    130                 135                 140

Glu Glu Ile Ala His Gly His Ile His Gln Glu Gly Gly Cys Cys Gly
145                 150                 155                 160

Gly His His His Asp Ser Asp Glu Glu Gly His Gly Cys Gly Cys Gly
                165                 170                 175

Ser His His His His Glu His Glu His Ala His Asp Gly Cys Cys
            180                 185                 190

Gly Asn Gly Gly Cys Lys His
            195

<210> SEQ ID NO 9
<211> LENGTH: 487
<212> TYPE: PRT
<213> ORGANISM: Artificial Sequence
<220> FEATURE:
<223> OTHER INFORMATION: Synthetic

<400> SEQUENCE: 9

Ala Asp Lys Ile Ala Ile Val Asn Met Gly Ser Leu Phe Gln Gln Val
1               5                   10                  15

Ala Gln Lys Thr Gly Val Ser Asn Thr Leu Glu Asn Glu Phe Arg Gly
            20                  25                  30

Arg Ala Ser Glu Leu Gln Arg Met Glu Thr Asp Leu Gln Ala Lys Met
        35                  40                  45

Lys Lys Leu Gln Ser Met Lys Ala Gly Ser Asp Arg Thr Lys Leu Glu
    50                  55                  60

Lys Asp Val Met Ala Gln Arg Gln Thr Phe Ala Gln Lys Ala Gln Ala
65                  70                  75                  80

Phe Glu Gln Asp Arg Ala Arg Arg Ser Asn Glu Glu Arg Gly Lys Leu
                85                  90                  95

Val Thr Arg Ile Gln Thr Ala Val Lys Ser Val Ala Asn Ser Gln Asp
            100                 105                 110

Ile Asp Leu Val Val Asp Ala Asn Ala Val Ala Tyr Asn Ser Ser Asp
        115                 120                 125

Val Lys Asp Ile Thr Ala Asp Val Leu Lys Gln Val Lys Gly Gly Gly
    130                 135                 140

Ser Gly Gly Gly Ser Gly Gly Gly Ser Gly Gly Ser Gly Gly Gly
145                 150                 155                 160

Ser Gly Gly Gly Ser Glu Ser Val Gln Ser Asn Ser Ala Val Leu Val
                165                 170                 175

His Phe Thr Leu Lys Leu Asp Asp Gly Thr Thr Ala Glu Ser Thr Arg
            180                 185                 190

Asn Asn Gly Lys Pro Ala Leu Phe Arg Leu Gly Asp Ala Ser Leu Ser
        195                 200                 205

Glu Gly Leu Glu Gln His Leu Leu Gly Leu Lys Val Gly Asp Lys Thr
    210                 215                 220

Thr Phe Ser Leu Glu Pro Asp Ala Ala Phe Gly Val Pro Ser Pro Asp
225                 230                 235                 240

Leu Ile Gln Tyr Phe Ser Arg Arg Glu Phe Met Asp Ala Gly Glu Pro
                245                 250                 255

Glu Ile Gly Ala Ile Met Leu Phe Thr Ala Met Asp Gly Ser Glu Met
            260                 265                 270

-continued

```
Pro Gly Val Ile Arg Glu Ile Asn Gly Asp Ser Ile Thr Val Asp Phe
        275                 280                 285

Asn His Pro Leu Ala Gly Gln Thr Val His Phe Asp Ile Glu Val Leu
    290                 295                 300

Glu Ile Asp Pro Ala Leu Glu Gly Gly Ser Gly Gly Gly Ser Gly
305                 310                 315                 320

Gly Gly Ser Gly Gly Gly Ser Gly Gly Gly Ser Gly Gly Gly Ser Glu
            325                 330                 335

Ser Val Gln Ser Asn Ser Ala Val Leu Val His Phe Thr Leu Lys Leu
            340                 345                 350

Asp Asp Gly Thr Thr Ala Glu Ser Thr Arg Asn Asn Gly Lys Pro Ala
            355                 360                 365

Leu Phe Arg Leu Gly Asp Ala Ser Leu Ser Glu Gly Leu Glu Gln His
    370                 375                 380

Leu Leu Gly Leu Lys Val Gly Asp Lys Thr Thr Phe Ser Leu Glu Pro
385                 390                 395                 400

Asp Ala Ala Phe Gly Val Pro Ser Pro Asp Leu Ile Gln Tyr Phe Ser
                405                 410                 415

Arg Arg Glu Phe Met Asp Ala Gly Glu Pro Glu Ile Gly Ala Ile Met
                420                 425                 430

Leu Phe Thr Ala Met Asp Gly Ser Glu Met Pro Gly Val Ile Arg Glu
            435                 440                 445

Ile Asn Gly Asp Ser Ile Thr Val Asp Phe Asn His Pro Leu Ala Gly
            450                 455                 460

Gln Thr Val His Phe Asp Ile Glu Val Leu Glu Ile Asp Pro Ala Leu
465                 470                 475                 480

Glu His His His His His His
                485
```

CHAPERONE-CHAPERONE FUSION POLYPEPTIDES FOR REDUCTION OF INTERFERENCE AND STABILIZATION OF IMMUNOASSAYS

RELATED APPLICATIONS

This application is a continuation of International Patent Application No. PCT/EP2013/068269 filed Sep. 4, 2013, and claims priority to EP Patent Application No. 12006298.9 filed Sep. 6, 2012, the disclosures of which are hereby incorporated by reference in their entirety.

FIELD OF THE INVENTION

The invention concerns a fusion polypeptide comprising several molecules of folding helper polypeptides, comprising one multimerization domain, in particular Skp, and at least one molecule of SlyD or SlpA, wherein no further target polypeptide sequences are fused to said fusion polypeptide. The invention further concerns an immunoassay and the use of said fusion polypeptide in an immunoassay for reduction of interferences or minimizing false positive results or for stabilizing proteinaceous assay reagents. Further the invention concerns a reagent kit for use in an immunoassay comprising said fusion polypeptide.

BACKGROUND OF THE INVENTION

Chaperones, which are known as classical folding helpers, are proteins that assist the folding and maintenance of the structural integrity of other proteins. They bind to denatured or hydrophobic surfaces of proteins and help in re-naturing and keeping proteins in solution. Due to their superior physico-chemical properties chaperones are used as folding assistants and fusion partners in protein technology. One class of chaperones is the family of FKBP chaperones, proteins that bind to the immunosuppressant drug FK506.

The use of FKBP chaperones like SlyD, FkpA and SlpA (=SlyD-like protein A) as fusion partners for difficult proteins has been widely described (WO 2003/000878, WO 2009/074318, EP 2127679).

Commercially available immunoassays for the detection of antibodies against pathogens like, e.g., human immunodeficiency virus (HIV), Rubella virus, cytomegalovirus (CMV) or herpes simplex virus (HSV) contain polypeptide fusion proteins wherein chaperones are fused to specific target antigen sequences. Such fusion proteins are described in, e.g., Scholz et al., J. Mol. Biol. (2005) 345, 1229-1242, Scholz et al., Biochemistry (2006) 45, 20-33 or Scholz et al., Biochemistry (2008) 47, 4276-4287.

SlyD, FkpA and SlpA possess outstanding solubilization (i.e. chaperone) properties and are characterized in that they are able to refold reversibly after chemically or thermally induced unfolding. As fusion partners for difficult target polypeptides they play at least a threefold role: firstly, they increase the production of target proteins that are heterologously overexpressed in procaryotic organisms, secondly, they facilitate and assist the in vitro refolding of the target polypeptides, and thirdly, they increase the overall solubility and stability of the respective target polypeptide.

However, chaperones like SlyD, FkpA and SlpA are immunogens in their own right. Since they are abundant bacterial proteins, they are recognized as non-self by the human (or, generally speaking, mammalian) immune system, triggering a powerful humoral immune response, which results in the production of specific antibodies with high affinity. A considerable percentage of adult human sera therefore contain significant immunoglobulin titers against these chaperones. As a consequence, there is a considerable likelihood that a human serum sample may turn out false positive in an immunoassay, in particular in an immunoassay of the double antigen sandwich format that uses antigen specifiers fused to bacterial chaperone modules.

In order to avoid such unwanted cross-reactions due to the antibody-induced bridging of fusion partners, immunoassays are usually designed in an asymmetric fashion. This means that for example in an immunoassay for the detection of antibodies designed in the well-known double antigen sandwich format (DAGS) a person skilled in the art uses different fusion partners for the applied antigens on both sides of the assay in order to avoid non-specific bridging. If identical fusion partners were used for the antigens on the solid phase and the detection side, interfering components in the sample could establish a bridge between said identical fusion partners and thus evoke a (false) positive reaction.

As a further means to prevent unwanted binding to a fusion partner which is part of an antigen-fusion protein, a chemically polymerized form of the employed fusion module (i.e. the fusion part without any specific antigen) is usually added to the assay in large excess. Due to their high epitope density and their high effective concentrations, these chemically polymerized fusion modules preferably allure, bind and quench those IgGs and IgMs that are directed towards said fusion module. The chemically polymerized fusion modules serve as a bait, and they quench the interfering compounds in the sample very efficiently so that interferences can be suppressed and ruled out. When, for instance, E. coli SlyD is used as a fusion partner for a given antigen in an immunoassay of the double antigen sandwich type, it would be highly advisable to generate chemically polymerized E. coli SlyD (by means of cros slinking with, e.g., glutardialdehyde) and to add this polymer to the assay as an anti-interference substance.

However, a considerable disadvantage in using chemically polymerized proteins lies in the chemical production process itself. Depending on the cross-linking agent applied, the chemical polymerization process is not entirely reproducible. The chemically cross-linked polymers usually show a large distribution of polymers of different size, i.e. they strongly vary with respect to connectivity and they are characterized by considerable heterogeneities. In order to select the effective polymer fractions (i.e. the polymer fractions with the desired anti-interference abilities) the polymer pool needs to be purified and fractionated by time-consuming and cumbersome chromatographic methods. In addition, only limited yields can be obtained as only a small percentage of the product will elute in the desired fraction.

In order to overcome the obstacle of using insufficiently characterized chemically polymerized material in immunoassays we searched for an alternative way to generate anti-interference substances. We strived to obtain anti-interference modules with a sufficiently high and well-defined epitope density in a simple and convenient manner. So we addressed the question whether it was possible to create a well-defined, highly soluble and highly efficient anti-interference module in an utterly recombinant fashion. Briefly, the problem to be solved was to obtain chaperone fusion partners in a soluble form, with high epitope density and in a reproducible and standardizable way.

SUMMARY OF THE INVENTION

The problem is solved by the current invention as characterized by the claims. In particular, the invention concerns a fusion polypeptide comprising several molecules of folding helper polypeptides, comprising one multimerization domain and at least one molecule of SlyD or SlpA, wherein no further target polypeptide sequences are fused to said fusion polypeptide. As a preferred multimerization domain Skp is used. Preferably one molecule of Skp is fused to two adjacent molecules of SlyD or to two adjacent molecules of SlpA. In another preferred embodiment one molecule of Skp is N-terminally fused to two adjacent molecules of SlyD or to two adjacent molecules of SlpA or to another monomeric chaperone that serves as a fusion partner. The term "N-terminally fused" means that Skp is fused to the N-terminal end of another protein molecule, in this case to the N-terminal end of either SlyD or SlpA. In a further preferred mode the fusion polypeptide according to the invention comprises SEQ ID NO. 1 which can also be named Skp-tandem-SlyD or Skp-SlyD-SlyD. A preferred fusion polypeptide is a polypeptide consisting of SEQ ID NO. 1 (Skp-tandem-SlyD). A further preferred fusion polypeptide is a polypeptide comprising SEQ ID NO. 9 which can also be named Skp-tandem-SlpA or Skp-SlpA-SlpA. Particularly preferred is a polypeptide consisting of SEQ ID NO. 9.

Another embodiment of the invention is the use of a fusion polypeptide as an additive in an immunoassay or as an additive to an assay reagent so that the fusion polypeptide can be used for reduction of interferences or for minimizing false positive results. According to the invention said fusion polypeptide can also be used for increasing the solubility of proteinaceous ingredients within an assay reagent. Also encompassed by a further preferred embodiment of the invention is a reagent kit for the detection of an analyte in an isolated sample by an immunoassay which comprises said fusion polypeptide.

In a further preferred embodiment a method for detecting an analyte in an isolated sample is encompassed wherein a fusion polypeptide as characterized above is used as a reagent for reduction of interference or for minimizing false positive results.

Another embodiment of the invention is a method for detecting an analyte such as, e.g., an antibody in an isolated sample, said method comprising a) forming an immunoreaction admixture by admixing a body fluid sample with a specific binding partner that can be specifically bound by said analyte present in said sample b) adding a fusion polypeptide according to the invention to said immunoreaction admixture either before, at the same time or after said specific binding partner is added to said sample c) maintaining said immunoreaction admixture for a time period sufficient for allowing the analyte present in said body fluid sample to immunoreact with said specific binding partner to form an immunoreaction product; and d) detecting the presence and/or the concentration of any of said immunoreaction product.

A further aspect of the invention is a reagent kit for the detection of an analyte, in particular for the detection of an antibody, in an isolated sample by an immunoassay, said kit comprising a fusion polypeptide according to the invention. Other ingredients of a reagent kit are known to someone skilled in the art and include specific binding reagents such as e.g. antigens. Further kit components are buffers, preservatives, labeling substances and instructions for use.

BRIEF DESCRIPTION OF THE FIGURES

FIGS. 1 to 7 show tables 1a-c, 2a-c and 3 (see example 3), presenting results on anti-interference activity of the fusion polypeptides in an immunoassay for detection of HIV anti-gp41 antibodies.

FIG. 1 shows table 1a.
FIG. 2 shows table 1b.
FIG. 3 shows table 1c.
FIG. 4 shows table 2a.
FIG. 5 shows table 2b.
FIG. 6 shows table 2c.
FIG. 7 shows table 3.
FIG. 10 shows table 4, presenting results on anti-interference activity of the fusion polypeptides in an immunoassay for detection of anti-HSV2 antibodies (see example 4).

Figure 8:
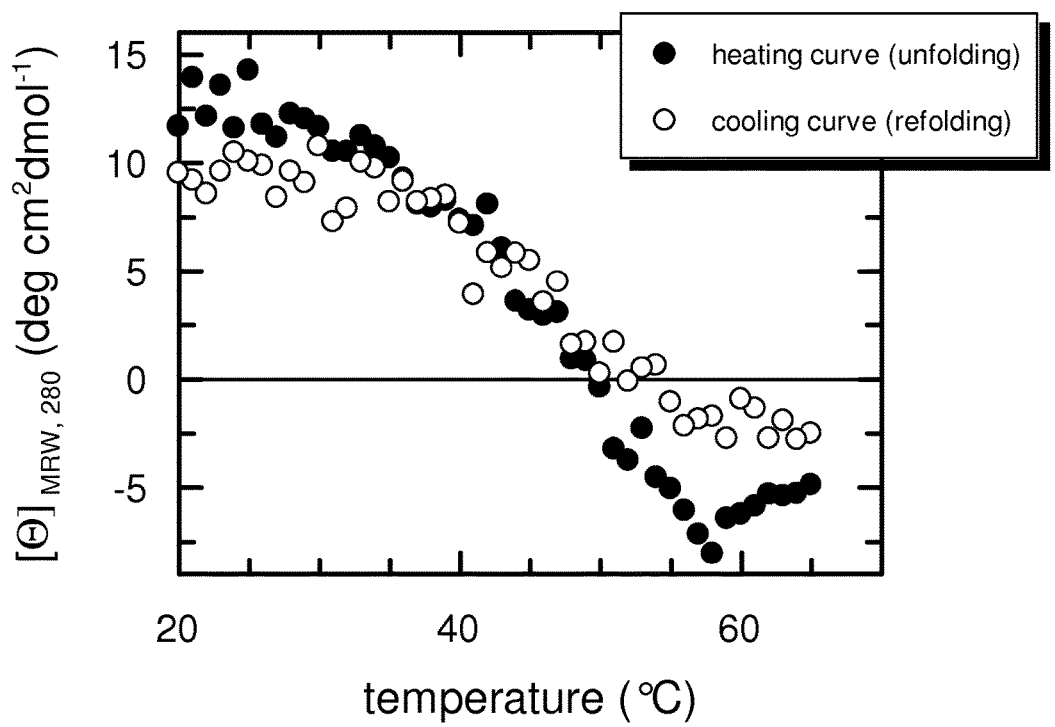
FIG. 8 shows the thermally induced unfolding and refolding of Skp-SlyD-SlyD as monitored in the near UV region at a detection wavelength of 280 nm.

SEQ ID NO. 1 shows the amino acid sequence of Skp-tandem-SlyD or Skp-SlyD-SlyD. The glycine-rich spacer region (underlined) between the Skp and SlyD units has been added to enable maximal flexibility of the fusion partners and to make sure that the Skp units may form ordered trimers without any interference of the C-terminally fused SlyD proteins. An additional C-terminal octa-histidine tag has been added for purification purposes (see experimental section). SEQ ID NO. 1 comprises amino acid residues 1-165 of *E. coli* SlyD (complete molecule cf. SEQ ID NO. 3) in tandem form, i.e. two *E. coli* SlyD (1-165) units in a row.

```
ADKIAIVNMG SLFQQVAQKT GVSNTLENEF RGRASELQRM

ETDLQAKMKK LQSMKAGSDR TKLEKDVMAQ

RQTFAQKAQA FEQDRARRSN EERGKLVTRI QTAVKSVANS

QDIDLVVDAN AVAYNSSDVK DITADVLKQV

KGGGSGGGSG GGSGGGSGGG SGGGMKVAKD LVVSLAYQVR

TEDGVLVDES PVSAPLDYLH GHGSLISGLE

TALEGHEVGD KFDVAVGAND AYGQYDENLV QRVPKDVFMG

VDELQVGMRF LAETDQGPVP VEITAVEDDH

VVVDGNHMLA GQNLKFNVEV VAIREATEEE LAHGHVHGAH

DHHHDHDHDG GGSGGGSGGG SGGGSGGGSG

GGMKVAKDLV VSLAYQVRTE DGVLVDESPV SAPLDYLHGH

GSLISGLETA LEGHEVGDKF DVAVGANDAY

GQYDENLVQR VPKDVFMGVD ELQVGMRFLA ETDQGPVPVE

ITAVEDDHVV VDGNHMLAGQ NLKFNVEVVA

IREATEEELA HGHVHGAHDH HHDHDHDGGG SHHHHHHHH
```

SEQ ID NO. 2 shows the complete amino acid sequence of *E. coli* Skp (161 aa) according to SwissProt Accession No. P11457. For the fusion polypeptide according to the invention, the signal sequence of *E. coli* Skp (aa 1-20) is removed in order to make sure that the target molecule is produced and retained in the cytosol of the overproducing prokaryotic host. Preferably, the mature form of *E. coli* Skp, i.e. aa 21-161 of the sequence listed below is used.

```
MKKWLLAAGL GLALATSAQA ADKIAIVNMG SLFQQVAQKT

GVSNTLENEF KGRASELQRM ETDLQAKMKK
```

-continued

LQSMKAGSDR TKLEKDVMAQ RQTFAQKAQA FEQDRARRSN

EERGKLVTRI QTAVKSVANS QDIDLVVDAN AVAYNSSDVK

DITADVLKQV K

SEQ ID NO. 3 represents the complete *E. coli* SlyD amino acid sequence (196 amino acid residues) which is also accessible via ID P0A9K9 in the SwissProt database. For the fusion polypeptide according to the invention, preferably a C-terminally truncated version of *E. coli* SlyD spanning amino acid residues 1-165 of the sequence listed below is used.

MKVAKDLVVS LAYQVRTEDG VLVDESPVSA PLDYLHGHGS

LISGLETALE GHEVGDKFDV AVGANDAYGQ

YDENLVQRVP KDVFMGVDEL QVGMRFLAET DQGPVPVEIT

AVEDDHVVVD GNHMLAGQNL KFNVEVVAIR

EATEEELAHG HVHGAHDHHH DHDHDGCCGG HGHDHGHEHG

GEGCCGGKGN GGCGCH

SEQ ID NO. 4 shows the amino acid sequence of the glycine-rich spacer (comprising triple glycine units separated by a serine) that can be used as a flexible, soluble and protease-resistant spacer or linker between several chaperone moieties.

GGGSGGGSGG GSGGGSGGGS GGG

SEQ ID NO. 5 shows the amino acid sequence of the octa-histidine tag or "His-tag" (comprising eight histidine units) that can be added to the C-terminal end of a protein to allow Ni-NTA assisted protein purification.

GGGSHHHHHH HH

SEQ ID NO: 6 shows the complete amino acid sequence of FkpA (270 aa), accessible also via the SwissProt database Accession No. P45523. For the fusion polypeptide according to the invention the signal sequence of *E. coli* FkpA (aa 1-25) is removed in order to make sure that the target molecule is produced and retained in the cytosol of the overproducing prokaryotic host. Preferably, the mature form of *E. coli* FkpA, i.e. aa 26-270 of the sequence listed below is used.

MKSLFKVTLL ATTMAVALHA PITFAAEAAK PATAADSKAA

FKNDDQKSAY ALGASLGRYM

ENSLKEQEKL GIKLDKDQLI AGVQDAFADK SKLSDQEIEQ

TLQAFEARVK SSAQAKMEKD

AADNEAKGKE YREKFAKEKG VKTSSTGLVY QVVEAGKGEA

PKDSDTVVVN YKGTLIDGKE

FDNSYTRGEP LSFRLDGVIP GWTEGLKNIK KGGKIKLVIP

PELAYGKAGV PGIPPNSTLV

FDVELLDVKP APKADAKPEA DAKAADSAKK

SEQ ID NO. 7 shows the complete amino acid sequence (149 amino acids) of *E. coli* SlpA, taken from the SwissProt database accession no. P0AEM0.

MSESVQSNSA VLVHFTLKLD DGTTAESTRN NGKPALFRLG

DASLSEGLEQ HLLGLKVGDK

TTFSLEPDAA FGVPSPDLIQ YFSRREFMDA GEPEIGAIML

FTAMDGSEMP GVIREINGDS

ITVDFNHPLA GQTVHFDIEV LEIDPALEA

SEQ ID NO. 8 shows the amino acid sequence of *Pasteurella multocida* SlyD (full length) according to Swiss Prot ID: Q9CKP2

MKIAKNVVVS IAYQVRTEDG VLVDEAPVNQ PLEYLQGHNN

LVIGLENALE GKAVGDKFEV

RVKPEEAYGE YNENMVQRVP KDVFQGVDEL VVGMRFIADT

DIGPLPVVIT EVAENDVVVD

GNHMLAGQEL LFSVEVVATR EATLEEIAHG HIHQEGGCCG

GHHHDSDEEG HGCGCGSHHH

HEHEHHAHDG CCGNGGCKH

SEQ ID NO. 9 shows the amino acid sequence of Skp-tandem-SlpA or Skp-SlpA-SlpA. The glycine-rich spacer region (underlined) between the Skp and SlpA units has been added to enable maximal flexibility of the fusion partners and to make sure that the Skp units may form ordered trimers without any interference of the C-terminally fused SlpA proteins. An additional C-terminal hexa-histidine tag has been added for purification purposes. SEQ ID NO. 9 comprises amino acid residues 2-148 of *E. coli* SlpA (complete molecule cf. SEQ ID NO. 7, but lacking the N-terminal methionine and the C-terminal alanine) in tandem form, i.e. two *E. coli* SlpA (2-148) units in a row.

ADKIAIVNMG SLFQQVAQKT GVSNTLENEF RGRASELQRM

ETDLQAKMKK LQSMKAGSDR TKLEKDVMAQ

RQTFAQKAQA FEQDRARRSN EERGKLVTRI QTAVKSVANS

QDIDLVVDAN AVAYNSSDVK DITADVLKQV

KGGGSGGGSG GGSGGGSGGG SGGGSESVQS NSAVLVHFTL

KLDDGTTAES TRNNGKPALF RLGDASLSEG

LEQHLLGLKV GDKTTFSLEP DAAFGVPSPD LIQYFSRREF

MDAGEPEIGA IMLFTAMDGS EMPGVIREIN

GDSITVDFNH PLAGQTVHFD IEVLEIDPAL EGGGSGGGSG

GGSGGGSGGG SGGGSESVQS NSAVLVHFTL

KLDDGTTAES TRNNGKPALF RLGDASLSEG LEQHLLGLKV

GDKTTFSLEP DAAFGVPSPD LIQYFSRREF

MDAGEPEIGA IMLFTAMDGS EMPGVIREIN GDSITVDFNH

PLAGQTVHFD IEVLEIDPAL EHHHHHH

DETAILED DESCRIPTION OF THE INVENTION

In commercially available immunoassays using rare reagents that contain SlyD fusion modules usually chemically cross-linked chaperone molecules such as tandem SlyD (two molecules of SlyD, linked via a short peptidic sequence, polymerized by means of glutardialdehyde) are added for reduction of interferences. As mentioned in the background section, due to the production process these chemically cross-linked additives are rather heterogeneous and cannot be provided in a strictly reproducible way with satisfying yields.

Although the use of polypeptide fusion proteins wherein chaperones are fused to specific target antigen sequences has been described in great detail before (see background of the invention) prior art is silent about how to overcome interferences in immunoassays. WO 2003/000878 describes FkpA as a chaperone that exerts its function in form of oligomers that can be fused to target polypeptide sequences. EP 1982993 discloses fusion polypeptides comprising at least one multimerization domain and a plurality of copies of an epitope segment from a pathogen. These polypeptides are applied as specific antigenic target sequences. However, the problem of eliminating interferences due to cross-reacting antibodies that bind to the chaperone modules and thus cause false positive results has hitherto not been addressed.

Surprisingly, by fusing a chaperone multimerization domain to at least one molecule of SlyD or SlpA we have been able to produce highly effective anti-interference agents. On top of that, in certain sera a significant background signal suggestive of a positive result cannot be minimized or suppressed effectively by the chemically cross-linked prior art reagent whereas the fusion polypeptide according to the invention is able to suppress the high background signal by reducing the interference. When added as an anti-interference agent to samples, none of the true positive samples are significantly affected, i.e. true positive samples comprising anti-HIV antibodies are invariably detected as positive samples.

Unexpectedly, by fusing a chaperone multimerization domain to at least one molecule of SlyD or SlpA we have been able to produce a well-folded, highly soluble artificial chimeric protein which forms regular trimers. It is far from self-evident that fusion of two chaperones via a flexible linker segment yields a soluble and functional protein in which the constituents largely maintain their genuine properties. Since chaperones such as Skp, SlyD and SlpA possess polypeptide binding sites which have been evolved to recognize and reversibly bind hydrophobic protein surfaces, and since these polypeptide binding sites are, themselves, hydrophobic by nature, it would have been very likely that the polypeptide binding sites of the two chaperones bind and saturate each other, leading to locked complexes with limited value for epitope-presenting purposes. It also would have been conceivable that fusion of two (sterically demanding) SlyD units to the C-terminal end of Skp compromises the structural integrity of Skp and, possibly, abolishes the intrinsic trimerization of Skp.

However, what we find is that Skp-SlyD, Skp-SlyD-SlyD and Skp-SlpA-SlpA indeed form regular trimers which are highly stable and soluble and which show—even though they are oligomeric—largely reversible folding behavior. It also would have been conceivable that the solubility of the artificial fusion polypeptide (i.e. the combination of two unrelated chaperones) turns out to be poor due to the high effective concentration of the hydrophobic polypeptide binding regions which are brought into close proximity by covalent fusion of Skp and SlyD or SlpA, respectively. Surprisingly to us, the converse is true: Skp-SlyD-SlyD possesses an outstanding solubility and it can be concentrated to >100 mg/ml (in 50 mM potassium phosphate pH 7.0, 250 mM KCl, 0.5 mM EDTA) without any tendency to aggregate. When Skp-SlyD-SlyD from such a concentrated solution is subjected to analytical gel filtration on a Superdex 200 column, the fusion polypeptide elutes in a single symmetric peak pointing to a perfectly soluble and stable trimer.

Skp-SlyD-SlyD is not only highly soluble, but its refolding behavior is also reversible. This is highlighted by the fact that we were able to elaborate a purification protocol which includes the step of matrix-coupled refolding: The target molecule is bound in an unfolded form to a Ni-NTA support via its C-terminal octa-histidine tag. While it remains bound to the solid support, it is refolded by a simple buffer change. Subsequently, the refolded protein is eluted by an imidazole pulse. Surprisingly to us, upon imidazole elution, the eluted Skp-SlyD-SlyD monomers form soluble trimers almost quantitatively. To us, it is astounding that the matrix-coupled refolding of a trimeric protein such as Skp-SlyD-SlyD works so well and with impressively high yields. We find that the same holds true for Skp-SlpA-SlpA: very similar to Skp-SlyD-SlyD, Skp-SlpA-SlpA can be obtained in large amounts from an *E. coli* overproducing strain and it can be renatured in a well-ordered trimeric form by matrix-assisted refolding. And, quite similar to its SlyD counterpart, Skp-SlpA-SlpA is highly soluble and possesses very favourable physicochemical properties.

According to the invention the obtained fusion polypeptide—unlike the fusion polypeptides described in prior art—is free of further target polypeptide antigenic sequences as the fusion polypeptide is used for interference reduction or protein stabilization. It is not applied as a specific antigenic polypeptide for binding to analyte molecules such as antibodies. It is important that the analyte present in the sample—like e.g. antibodies against a pathogen—does not bind to the fusion polypeptide of the invention. Therefore target polypeptide sequences like antigen sequences derived from mammalian pathogens like viruses, bacteria, single-cell or multi-cell parasites are not part of the fusion polypeptide.

The fusion polypeptide according to the invention can be obtained in a reproducible way in homogeneous fractions with high yields. It possesses a well-defined epitope density which is necessary and sufficient to recognize, bind and quench interference factors of the IgG and IgM type. The fusion polypeptide is able to suppress false positive reactions in an immunoassay in a way that is not only equivalent but superior to the chemically produced reagent of prior art. Its production process is straightforward, simple and easy to standardize and inevitably results in high yields of a well-defined homogeneous fusion polypeptide with outstanding anti-interference properties.

According to the invention the fusion polypeptide preferably contains one multimerization domain. A multimerization domain is a domain that mediates and supports non-covalent association of several protein subunits containing that very multimerization domain. For example, a dimerization domain is a domain that triggers association of two subunits, a trimerization domain is a domain that supports non-covalent association of three subunits and so on.

The second part of the fusion polypeptide is at least one molecule of SlyD, preferably *E. coli* SlyD, but SlyD molecules from other organisms, such as, e.g., *Pasteurella*

*multocida* SlyD (cf. SEQ ID NO. 8) can also be used. Further preferred is a fusion polypeptide wherein one molecule of Skp is fused to two adjacent molecules of SlyD. In another embodiment of the invention other monomeric chaperones such as SlpA are also suitable as fusion partners which are fused to the single multimerization domain.

A further aspect of the invention is the use of the fusion polypeptides described above for reduction of interferences or for minimizing false positive results. The fusion polypeptide of the invention can be added to the immunoassay admixture (comprising sample and a binding partner specifically binding to the analyte in the sample) either before, at the same time or after said specific binding partner is added to the sample. Preferably, the fusion polypeptide is added to the test reagents before the body fluid sample containing the analyte, e.g. an antibody, is brought into contact with the specific binding partners (in this case the specific binding partners would be antigens).

Various formats and principles of immunoassays for detecting analytes and different modes of detection have been widely described and are familiar to a person skilled in the art. Of particular interest are immunoassays in which the analyte is an antibody. Preferably the immunoassay according to the invention detects antibodies against mammalian viral or bacterial pathogens such as e.g. hepatitis A, B or C virus, HIV (human immunodeficiency virus), HSV (herpes simplex virus), HTLV (human T-cell leukemia virus), EBV (Epstein-Barr virus), Rubella virus, CMV (cytomegalovirus), Treponema pallidum or Borrelia burgdorferi.

The invention is further illustrated in the examples section.

EXAMPLES

Example 1: Manufacture of Fusion Polypeptides

Cloning and Purification of Skp/SlyD Chaperone Fusion Polypeptides
Cloning of Expression Cassettes
In order to generate a suitable expression construct, an expression cassette encoding EcSkp-EcSlyD-EcSlyD was ligated into expression plasmid pQE80L (Qiagen, Hilden, Germany) by a two-step cloning strategy.

The sequence of the *E. coli* Skp (EcSkp) was retrieved from the SwissProt database (SwissProt ID P0AEU7). In a first step, a synthetic gene comprising the Shine-Dalgarno sequence from expression vector pQE80L, the coding sequence of the mature Skp chaperone amino acids 21-161 (the signal peptide spanning amino acid residues 1-20 were omitted, the ATG start codon (methionine) was added in frame), with a part of a glycine-rich linker region as well as suitable recognition sites for restriction endonucleases EcoRI (5' end) and BamHI (3' end), was purchased from Sloning (Vaterstetten, Germany). The synthetic 489 bp DNA fragment was hydrolyzed with the respective restriction endonucleases and ligated into the EcoRI/BamHI opened expression vector pQE80L under control of a T5 promoter ($P_{T5}$).

Secondly, a further synthetic gene encoding two *E. coli* SlyD units (EcSlyD, residues 1-165, SwissProt accession no. P0A9K9) connected via a glycine-rich linker region and encompassing part of a further linker region at the N-terminus as well as an octa-His-tag linked with a GGGS motif to the C-terminus was likewise purchased from Sloning (Vaterstetten, Germany). BamHI and HindIII restriction sites were added at the 5' and 3' ends of this cassette, respectively. Genes and restriction sites were designed to enable the in frame fusion of the EcSlyD-EcSlyD part to the 5' end of the EcSkp part by simple ligation. Therefore, the 1146 bp spanning fragment was hydrolyzed with restriction endonucleases BamHI and HindIII and ligated into the BamHI/HindIII opened, Skp containing vector pQE80L.

After ligation, competent cells of *E. coli* XL1Blue (Stratagene, La Jolla, Calif., USA) were transformed with the respective DNA. After plasmid preparation from suitable transformants, the correctness of the expression construct was reconfirmed by sequence analysis. The resulting expression plasmid has been named pQE80Skp-diSlyD.

The drawing below displays a scheme of the full length fusion polypeptide EcSkp-EcSlyD-EcSlyD comprising one *E. coli* Skp chaperone unit and two *E. coli* SlyD chaperone units connected by glycine rich linker regions and followed by a C-terminal octa-His-tag to allow Ni-NTA assisted protein purification.

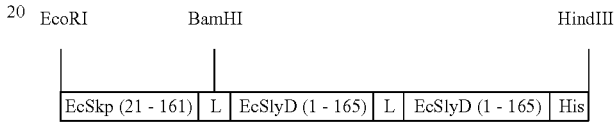

L = (GGGS)$_5$GGG (glycine rich linker region), see SEQ ID NO.: 4
His = GGGSHHHHHHHH (His-tag), see SEQ ID NO.: 5

The complete amino acid sequence of the desired fusion polypeptide is shown in SEQ ID No. 1.

The expression cassettes encoding the iterative SlyD constructs (SlyD, SlyD-SlyD, SlyD-SlyD-SlyD . . . ) have been cloned as described in Biochemistry (2006) 45, 20-33. The expression cassette encoding the Skp-SlpA-SlpA fusion polypeptide has been generated according to Scholz et al., J. Mol. Biol. (2005) 345, 1229-1242.

Recombinant Expression of EcSkp-EcSlyD-EcSlyD in an *E. coli* Host

In order to obtain the putative anti-interference polypeptide in sufficient amounts, EcSkp-EcSlyD-EcSlyD was recombinantly expressed in *E. coli*. For this purpose, competent cells of *E. coli* BL21 Codon+ (Merck (Novagen®), Darmstadt, Germany) were transformed with the generated expression construct pQE80Skp-diSlyD.

50 mL of SB medium (32.0 g tryptone, 20.0 g yeast extract, 5.0 g NaCl, ad 1000 mL A. dest.) supplemented with ampicillin (100 μg/mL) were inoculated with a single colony harboring the pQE80Skp-diSlyD plasmid and incubated over night at 37° C. (250 rpm). Subsequently, 1.5 L of SB medium (+100 μg/mL ampicillin) was inoculated with the overnight culture up to an O.D.$_{600}$ of ~0.5. At an O.D.$_{600}$ of ~3.0, cytosolic overexpression was induced by adding 0.5 mM isopropyl-β-D-thiogalactoside (IPTG) to the culture. Four hours after induction, cells were harvested by centrifugation (20 min at 6000 g) and stored at −20° C.

Aliquots of 0.4 O.D.$_{600}$ were taken before and four hours after induction and whole cell extracts were tested for expression of EcSkp-EcSlyD-EcSlyD by SDS-PAGE analysis. Overproduction of the target molecule was found to be highly abundant.

Overexpression of the SlyD and SlpA fusion proteins was carried out as described in Scholz et al., J. Mol. Biol. (2005) 345, 1229-1242 and Scholz et al., Biochemistry (2006) 45, 20-33.

Purification of Skp/SlyD/SlpA Polypeptide Fusions
The Skp/SlyD polypeptide fusions and the SlyD and SlpA fusion proteins were purified by using virtually identical protocols. For cell lysis, the frozen pellet was resuspended in chilled 50 mM sodium phosphate pH 8.0, 7.0 M GdmCl, 5 mM imidazole and the suspension was stirred for at least 2 h on ice to complete cell lysis. After centrifugation and filtration (0.45 μm/0.2 μm), the crude lysate was applied onto a Ni-NTA column equilibrated with the lysis buffer including 5.0 mM TCEP. The subsequent washing step was tailored for the respective target protein and ranged from 5 to 15 mM imidazole (in 50 mM sodium phosphate pH 8.0, 7.0 M GdmCl, 5.0 mM TCEP). At least 10-15 volumes of the washing buffer were applied. Then, the GdmCl solution was replaced by 50 mM potassium phosphate pH 8.0, 100 mM KCl, 10 mM imidazole, 5.0 mM TCEP to induce conformational refolding of the matrix-bound protein. In order to avoid reactivation of copurifying proteases, a protease inhibitor cocktail (Complete® EDTA-free, Roche) was included in the refolding buffer. A total of 15-20 column volumes of refolding buffer were applied in an overnight reaction. Then, both TCEP and the Complete® EDTA-free inhibitor cocktail were removed by washing with 3-5 column volumes 50 mM potassium phosphate pH 8.0, 100 mM KCl, 10 mM imidazole. Subsequently, the imidazole concentration—still in 50 mM potassium phosphate pH 8.0, 100 mM KCl—was raised to 60-70 mM for the EcSkp-EcSlyD fusion proteins, to 50 mM for EcSkp-EcSlpA-EcSlpA and to 30 mM for the SlyD fusion polypeptides in order to remove unspecifically bound protein contaminants. The native protein was then eluted by 500 mM imidazole in the same buffer. Protein-containing fractions were assessed for purity by Tricine-SDS-PAGE and pooled. Finally, the proteins were subjected to size-exclusion-chromatography (Superdex HiLoad, Amersham Pharmacia) and the protein-containing fractions were pooled and concentrated to 10-20 mg/ml in an Amicon cell (YM10). After the coupled purification and refolding protocol, protein yields of roughly 15-25 mg could be obtained from 1 g of *E. coli* wet cells, depending on the respective target protein.

Example 2

Spectroscopic Measurements

Protein concentration measurements were performed with an Uvikon XL double-beam spectrophotometer. The molar extinction coefficients ($\varepsilon_{280}$) were determined by using the procedure described by Pace (1995), Protein Sci. 4, 2411-2423. For EcSkp-EcSlyD-EcSlyD, a molar extinction coefficient ($\varepsilon_{M280}$) of 13410 $M^{-1}$ $cm^{-1}$ was used, for EcSkp-EcSlyD a molar extinction coefficient ($\varepsilon_{M280}$) of 7450 $M^{-1}$ $cm^{-1}$ was used. For EcSkp-EcSlpA-EcSlpA, a molar extinction coefficient ($\varepsilon_{M280}$) of 4470 $M^{-1}$ $cm^{-1}$ was used. For the repetitive *E. coli* SlyD constructs, SlyD, SlyD-SlyD, SlyD-SlyD-SlyD, SlyD-SlyD-SlyD-SlyD and SlyD-SlyD-SlyD-SlyD-SlyD, molar extinction coefficients of 5960 $M^{-1}$ $cm^{-1}$, 11920 $M^{-1}$ $cm^{-1}$, 17880 $M^{-1}$ $cm^{-1}$, 23840 $M^{-1}$ $cm^{-1}$ and 29800 $M^{-1}$ $cm^{-1}$ were used.

Example 3

Anti-Interference Activity of the SlyD Polypeptide Fusion Proteins

The anti-interference activity of the SlyD polypeptide fusion proteins was assessed in an automated Elecsys® 2010 analyzer (Roche Diagnostics GmbH). Elecsys® is a registered trademark of the Roche group. Measurements were carried out in the double antigen sandwich format.

Signal detection in Elecsys® 2010 is based on electrochemoluminescence. The biotin-conjugate (i.e. the capture-antigen) is immobilized on the surface of a streptavidin coated magnetic bead whereas the detection-antigen bears a complexed Ruthenium cation (switching between the redox states 2+ and 3+) as the signaling moiety. In the presence of a specific immunoglobulin analyte, the chromogenic ruthenium complex is bridged to the solid phase and emits light at 620 nm after excitation at a platinum electrode. The signal output is in arbitrary light units.

The recombinant anti-interference SlyD polypeptides were assessed in a double antigen sandwich (DAGS) immunoassay format. To this end, FkpA-FkpA-gp41 and SlyD-SlyD-gp41 as disclosed in EP 1 402 015 were used as biotin and ruthenium conjugates, respectively, to specifically detect anti-gp41 antibodies in human sera. gp41 is the immunodominant antigen of HIV, and soluble variants of the gp41 ectodomain—as disclosed in EP 1 402 015—are invaluable tools for the detection of HIV infections. FkpA-FkpA-gp41-biotin and SlyD-SlyD-gp41-ruthenium were used in R1 (reagent buffer 1) and R2 (reagent buffer 2) at concentrations of 750 ng/ml each.

In a first experiment, Trina sera negative for HIV were assessed with the aforementioned DAGS immunoassay setup. In order to get a hint to the incidence rate of false positives, the assessment was performed in the absence and in the presence of SS-Helix(GDA,P), a GDA-crosslinked soluble heterogeneous SlyD polymer which is used as an anti-interference substance. SS-Helix (GDA,P) was added to R1 (reagent buffer 1 containing the biotin conjugate) in large excess amounts (25 μg/ml). 60 μl R1 (reagent buffer 1, biotin conjugate and anti-interference SlyD polymer), 60 μl R2 (reagent buffer 2, ruthenium conjugate), 30 μl sample (human serum) and 50 μl bead suspension are then mixed and incubated to yield a reaction volume of roughly 200 μl.

Tables 1a-c (FIGS. 1-3) demonstrate the high incidence rate of elevated (false positive) signals in the absence of the anti-interference polymer. Even though two different chaperones, such as SlyD and FkpA, are used on the two sides of the double antigen sandwich immunoassay, we find a wealth of significantly elevated signals in a well-characterized panel of human sera (Trina Bioreactives AG, Nanikon, Switzerland) for which HIV infections have clearly been ruled out. The reason for this finding is that SlyD and FkpA, though different, are related molecules belonging to the FKBP family of chaperones and sharing a highly conserved FKBP domain. It is probably via this shared motif that the immunological cross-reaction takes place, evoking high signals and thus pretending a positive outcome in the HIV assay. Addition of the chemically polymerized anti-interference substance, SS-Helix(GDA,P) to the assay mixture reduces the elevated signals to normal negatives. Table 1c (FIG. 3) shows that even very strong interferences, i.e. high false positives, may be efficiently eliminated by addition of SS-Helix(GDA,P). The bottom line of the results shown in table 1a-c (FIGS. 1-3) is the following: interferences due to fusion partners in a DAGS immunoassay are frequent and they can efficiently be mitigated by the addition of cross-linked polymer variants of one fusion partner.

Tables 2a-c (FIGS. 4-6) illustrate the anti-interference capability of diverse recombinant SlyD variants. Five HIV negative sera, five anti-HIV positive sera and two false positive sera from a Trina panel (Trina Bioreactives AG, Nänikon, Switzerland) were assessed with FkpA-FkpA-gp41-biotin and SlyD-SlyD-gp41-ruthenium as described. The assays were performed in the absence and in the presence of diverse anti-interference candidates. The anti-interference modules under study were added to R1 (reagent buffer 1) at concentrations of 5 μg/ml and 25 μg/ml in order to reveal a possible dose effect. SS-Helix (GDA,P) was included in the experiment as a positive reference (i.e. a well-suited and potent anti-interference module). Without an anti-interference additive (Tab. 2a, V0), the signals of the false positive Trina sera amount to almost 60,000 counts, strongly suggestive of a high anti-gp41 antibody titer as a consequence of an HIV infection. Upon addition of SS-Helix (GDA,P), the false positive signals are, however, reduced to the level of the HIV negative sera (Tab. 2a, V1). When Skp-SlyD is added, the false positive signals are significantly reduced, too, but they still are elevated—even in the presence of 25 µg/ml—and would be strongly misleading, in that they indicate an HIV infection in an healthy individual (Tab. 2a, V2). When, however, Skp-SlyD-SlyD is added, the false positive signals are reduced to the signal level of the HIV negative sera (Tab. 2a, V3). Skp-SlyD-SlyD turns out to be as efficient as the chemically polymerized SS-Helix (GDA,P) in its anti-interference capacity. Obviously, the epitope density of Skp-SlyD-SlyD is high enough to efficiently bind to and quench interference factors which presumably belong to the IgM type of immunoglobulins. The equivalence (with respect to anti-interference) of a recombinantly produced module such as Skp-SlyD-SlyD with a crosslinked SlyD polymer such as SS-Helix (GDA,P) is an astounding outcome of our experiments.

In Tab. 2b (FIG. 5), two controls are shown: neither does addition of E. coli SlyD alone mitigate the false positive signals of the two Trina interference sera tested, nor does addition of E. coli Skp alone have any beneficial effects on the falsely elevated signals (Tab. 2b, V4 and V5). Even at concentrations as high as 25 µg/ml, none of the single components is able to affect the false positive signals. However, in combination, as a Skp-SlyD-SlyD fusion polypeptide, Skp and SlyD constitute a powerful anti-interference tool (Tab. 2a (FIG. 4), V3). The inability of the single monomeric E. coli SlyD to cope with the interferences of the Trina sera 16097448 and 47101943, strongly suggests that the respective interference factors belong to the M type of immunoglobulins (IgM). Obviously, a higher epitope density concomitant with a higher effective SlyD concentration is mandatory to efficiently bind to and quench the interference factors.

To critically challenge this assumption, we performed further anti-interference studies shown in table 2c (FIG. 6). As an analytical tool we used E. coli SlyD polymers that have been generated by standard cloning techniques as described in Biochemistry (2006) 45, 20-33. Put simply, E. coli SlyD units were joined by flexible, glycine- and serine-rich linkers to form a row. Up to five SlyD units were feasible in a single fusion polypeptide with satisfying expression yields in E. coli and convenient purification procedures.

Table 2c (FIG. 6) illustrates the need of a high SlyD epitope density for efficient anti-interference and it points to the fact that we can make use of the avidity effect (avidity means the high apparent affinity that occurs when a polyvalent binding molecule such as an IgM molecule encounters a polymeric substrate such as polymerized SlyD). Without any anti-interference additive, the signals of the Trina interference sera 16097448 and 47101943 amount to 59827 and 53491 counts, respectively, and clearly hint to the presence of anti-gp41 antibodies, even though the sera have unequivocally been confirmed as anti-HIV negative. When tandem SlyD (SlyD-SlyD) is added to R1 (reagent buffer 1) at a concentration of 25 µg/ml, the signals remain virtually unaffected (table 2c, V8). When triple SlyD (SlyD-SlyD-SlyD) is added to R1 at a concentration of 25 µg/ml, the signals are reduced to ~4000 counts (table 2c, V7). Although strongly quenched, the remaining signal still would pretend a positive result. When, however, penta-SlyD (SlyD-SlyD-SlyD-SlyD-SlyD) is added to R1 at a concentration of only 5 µg/ml, the signal reduction is comparable to the one achieved by the addition of chemically polymerized SS-Helix(GDA,P) at the same concentration (table 2a, V1; table 2c, V6). In other words, the anti-interference capacity of SlyD increases with the number of SlyD units that constitute the respective construct. The increase in anti-interference capacity is not linear, indicating that we are facing a cooperative rather than an additive effect.

In brief, Tab. 2 (FIGS. 4-6) shows that the anti-interference potential significantly increases with the number of the interconnected SlyD units. It suggests that at least five SlyD units in close proximity are necessary and sufficient for effective anti-interference. Penta-SlyD (SlyD-SlyD-SlyD-SlyD-SlyD) would thus be a promising anti-interference additive, but its expression yield in an E. coli host is rather poor and poses severe obstacles with respect to production upscaling. Skp-SlyD-SlyD is at least equivalent to SS-Helix (GDA,P) with respect to its anti-interference potential. Thus, the epitope density which is established by fusion of the trimeric Skp to tandem SlyD (SlyD-SlyD) is obviously sufficient to meet the requirement for efficient anti-interference. This is remarkable all the more since the availability of the recombinantly produced Skp-SlyD-SlyD module is much better and its production process is by far more reproducible and convenient.

Tab. 3 (FIG. 7) shows that, in some cases, the anti-interference capability of Skp-SlyD-SlyD is even superior to that of SS-Helix(GDA,P). Again, five negative sera, five anti-HIV positive sera and three interference sera with significantly elevated signals have been assessed in the Elecsys® 2012 automated analyzer. Without any anti-interference additive, the signals of the three interference sera amount to 10351, 1437 and 778 counts. When the crosslinked SlyD polymer SS-Helix (GDA,P) is added to R1 at a concentration of 20 µg/ml, the signals are only slightly reduced to values of 8042, 903 and 772 counts (Tab. 3, V1). When, however, Skp-SlyD-SlyD is added to R1 at concentrations of 5 µg/ml or 15 µg/ml, the signals are significantly reduced to the level of the negative sera, more precisely they are reduced to 566, 537 and 507 counts. It is noteworthy that addition of Skp-SlyD-SlyD has an obviously smoothing effect on the signals of the negative sera and that it slightly improves the coefficient of variation. This effect is more pronounced with Skp-SlyD-SlyD than it is with SS-Helix (GDA,P). To sum up, table 3 highlights the fact that Skp-SlyD-SlyD is, in some cases, superior to SS-Helix(GDA,P) in its anti-interference capability: In the case of the interference serum C133202 it reduces the signal from false positive to true negative. Even signals, which are only slightly elevated, as exemplified in the sera Pr149 or C133111, are significantly reduced to a signal level that closely approaches the blank value of the analyzer. On top of that, we observe a smoothing effect of Skp-SlyD-SlyD on the signals of the anti-HIV negative sera, leading to an overall decrease of the signals and an improved coefficient of variation.

Example 4

Anti-Interference Activity of the EcSkp-EcSlpA-EcSlpA Polypeptide Fusion Protein The anti-interference activity of EcSkp-EcSlpA-EcSlpA was assessed in an automated Elecsys® 2010 analyzer (Roche Diagnostics GmbH). Elecsys® is a registered trademark of the Roche group. Measurements were carried out in the double antigen sandwich format.

Signal detection in Elecsys® 2010 is based on electrochemoluminescence (for detailed explanation see example 3).

The recombinant EcSkp-EcSlpA-EcSlpA polypeptide was assessed in a double antigen sandwich (DAGS) immunoassay format. To this end, PmSlyD-mgG2 and EcSlpA-mgG2 as disclosed in EP 2 127 678 were used as biotin and ruthenium conjugates, respectively, to specifically detect anti-HSV-2 antibodies in human sera. Mature glycoprotein G2 (mgG2) is an immunodominant antigen of herpes simplex virus 2 (HSV-2), and soluble variants thereof—as disclosed in EP 2 127 678—are invaluable tools for the detection of HSV-2 infections. PmSlyD-mgG2-biotin and EcSlpA-mgG2-ruthenium conjugates were used in R1 (reagent buffer 1) and R2 (reagent buffer 2) at concentrations of 300 ng/ml each.

Anti-HSV-2 negative sera, anti-HSV-2 positive sera and anti-HSV-2 false positive sera (i.e. interference sera) were assessed with the aforementioned DAGS immunoassay setup. The assessment was performed in the absence and in the presence of EcSlpA-EcSlpA (GDA,P), a soluble heterogeneous GDA-crosslinked EcSlpA polymer which is used as an anti-interference substance in the anti-HSV-2 immunoassay. EcSlpA-EcSlpA (GDA,P) serves the role of an anti-interference benchmark: it constitutes the conventional anti-interference additive that has been generated by chemical crosslinking of an EcSlpA-EcSlpA polypeptide and that is well-suited to improve the specificity of immunoassays based on EcSlpA fusion antigens. The anti-interference additives under scrutiny were added to both R1 (reagent buffer 1, containing the biotin conjugate) and to R2 (reagent buffer 2, containing the ruthenium conjugate) in large excess amounts (10 μg/ml each). 70 μl R1 (reagent buffer 1, biotin conjugate and anti-interference EcSlpA polymer), 70 μl R2 (reagent buffer 2, ruthenium conjugate and anti-interference EcSlpA polymer), 20 μl sample (human serum) and 40 μl bead suspension are then mixed and incubated to yield a reaction volume of roughly 200 μl.

Even though two different chaperones, such as PmSlyD (i.e., SlyD from *Pasteurella multocida*) and EcSlpA (i.e., SlpA from *E. coli*), are used on the two sides of the double antigen sandwich immunoassay, significantly elevated signals are rather frequent in a panel of human sera, for which HSV-2 infections have clearly been ruled out. The reason for this finding is that the fusion partners PmSlyD and EcSlpA, although from different organisms, are related molecules belonging to the FKBP family of chaperones and sharing a highly conserved FKBP domain. It is probably via this shared motif that the immunological cross-reaction takes place, evoking high signals and thus pretending a positive outcome in the anti-HSV-2 assay. Addition of the chemically polymerized anti-interference substance, EcSlpA-EcSlpA (GDA,P), to the assay mixture reduces the elevated signals to normal negatives. Table 4 (FIG. 10) shows that even very strong interferences, i.e. high false positives [such as for sample 012], may be efficiently eliminated by addition of the anti-interference polymer EcSlpA-EcSlpA(GDA,P). As illustrated by table 4 (FIG. 10), interferences due to fusion partners in a DAGS immunoassay are frequent and they can efficiently be mitigated by the addition of crosslinked polymer variants of at least one of the fusion partners.

When EcSkp-EcSlpA-EcSlpA is added to the assay, we find that the false positive signals are reduced to the signal level of HSV-2 negative sera as well. Indeed, EcSkp-EcSlpA-EcSlpA turns out to be at least as efficient as the chemically polymerized EcSlpA-EcSlpA (GDA,P) in its anti-interference capacity. Obviously, the epitope density of Skp-EcSlpA-EcSlpA is high enough to efficiently bind to and quench interference factors which presumably belong to the IgM type of immunoglobulins. These interference sera are characterized in that they do not respond to the addition of monomeric anti-interference additives (see tab. 4/FIG. 10, samples 010 & 013). True positive signals are neither affected by the fusion polypeptide EcSkp-EcSlpA-EcSlpA nor by the chemically polymerized EcSlpA-EcSlpA (GDA, P). The equivalence (with respect to anti-interference) of a recombinantly produced module such as EcSkp-EcSlpA-EcSlpA with a crosslinked EcSlpA polymer such as EcSlpA-EcSlpA (GDA,P) is an astounding outcome of our experiments. In Tab. 4 (FIG. 10) two further controls are shown: EcSkp and EcSlpA (i.e. the components of the EcSkp-EcSlpA-EcSlpA fusion polypeptide) have been added to the immunoassay as single chaperones in order to assess their anti-interference capacity. The results are quite clear-cut: EcSkp alone does not affect the false positive signals of the interference sera at all. However, EcSlpA alone seems to exert a beneficial effect, at least in two out of four cases. As for the interference samples 011 and 012, addition of monomeric EcSlpA in large excess reduces the signal from 8204 to 969 counts and from 42168 to 14801 counts, respectively. One may conclude that the addition of monomeric EcSlpA might help to increase the assay specificity in some cases. Yet, comparison with EcSkp-EcSlpA-EcSlpA reveals at first glance that the fusion polypeptide is highly superior with respect to its anti-interference potential. Addition of EcSkp-EcSlpA-EcSlpA unambiguously reduces the false positives to true negatives, as shown in table 4 for the interference sera 010-013. It is remarkable that the recombinant-derived EcSkp-EcSlpA-EcSlpA fusion protein even outperforms the standard anti-interference additive EcSlpA-EcSlpA (GDA, P) with respect to its anti-interference activity (see table 4, samples 010, 011 and 013). Taken together with its ease of handling and production, the anti-interference features of EcSkp-EcSlpA-EcSlpA are outstanding and make this molecule a highly attractive additive in an immunoassay.

Example 5

CD-Detected Thermally Induced Unfolding of Skp-SlyD-SlyD

Near-UV CD spectra were recorded with a Jasco-720 spectropolarimeter with a thermostatted cell holder and converted to mean residue ellipticity. The buffer was 50 mM potassium phosphate pH 7.5, 250 mM KCl, 0.5 mM EDTA. The pathlength was 0.2 cm the protein concentration was 8.2 mg/ml (147 μM monomer, corresponding to 49 μM trimer). The range was 250-330 nm, the band width was 1.0 nm, the scanning speed was 20 nm/min at a resolution of 0.5 nm and the response was 1 s. In order to improve the signal-to-noise ratio, spectra were measured nine times and averaged.

Circular dichroism spectroscopy (CD) is the method of choice to assess both the secondary and the tertiary structure of proteins. Ellipticity in the aromatic region (250-330 nm) reports on tertiary contacts within a protein (i.e., the globular structure of a regularly folded protein) and is considered as the fingerprint region of a native-like fold (conformation).

Figure 9:
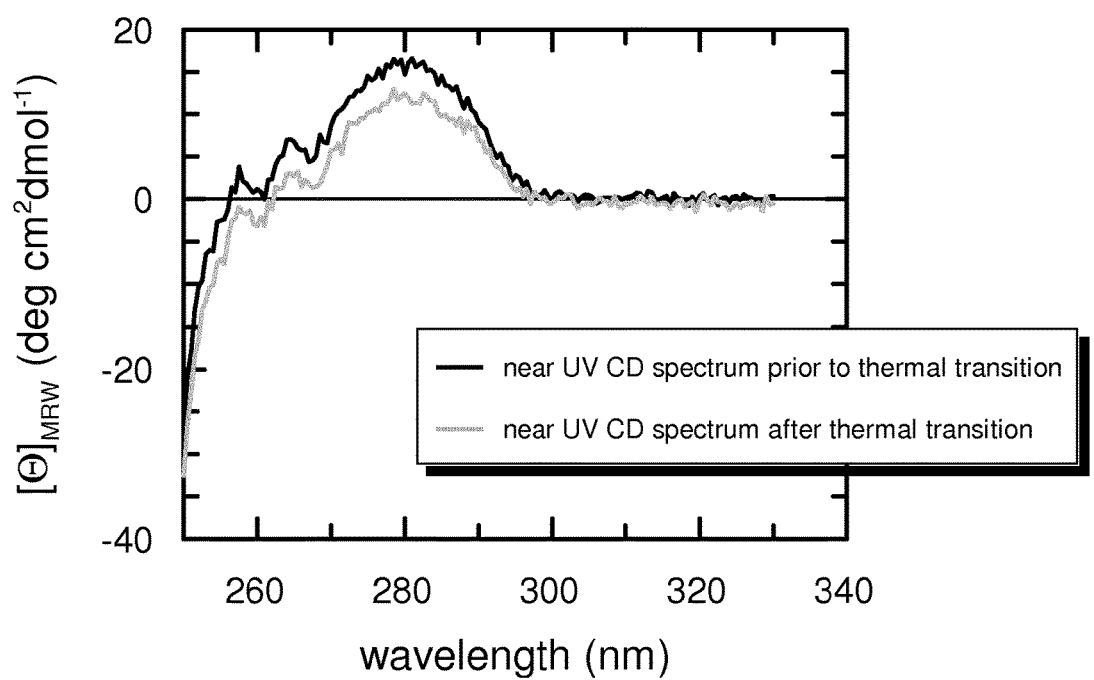
FIG. 9 shows near-UV CD spectra of Skp-SlyD-SlyD in the range of 250-330 nm (see example 5).

Near UV CD spectra of Skp-SlyD-SlyD were monitored to address the question whether the fusion protein adopts an ordered conformation after the matrix-coupled refolding procedure which is the crucial step in the purification process. The answer is quite clear-cut: the near UV CD signal of Skp-SlyD-SlyD unequivocally reports an orderly tertiary structure of the fusion polypeptide. The aromatic residues of Skp-SlyD-SlyD are obviously embedded in the lipophilic protein core and thus experience asymmetric surroundings which strongly points to a native-like conformation of both Skp and SlyD within the fusion construct (FIG. 9).

In order to address the question whether the thermally induced unfolding of Skp-SlyD-SlyD is reversible, melting curves were monitored in the near UV region at a detection wavelength of 280 nm. The temperature range was 20-65° C., the band width was 1.0 nm, the temperature slope was 1° C./min and the response was 4 s (see FIG. 8).

The thermally-induced unfolding was monitored at 280 nm (which is the wavelength of the maximal signal amplitude for Skp-SlyD-SlyD). Upon heating, the non-covalent contacts which stabilize the native conformation of the Skp-SlyD-SlyD molecule become loose and finally break down. This thermally induced unfolding is reflected in a decrease in the CD signal as shown in FIG. 8. At 60° C., Skp-SlyD-SlyD is fully unfolded. Strikingly, the CD signal comes back again when the protein solution is chilled down to 20° C. Despite a slight hysteresis, the unfolding curve and the refolding curve virtually superimpose, strongly indicative of a reversible refolding behavior of Skp-SlyD-SlyD (see FIG. 8). It is astounding that the thermally induced unfolding of a complex trimeric fusion protein such as Skp-SlyD-SlyD is—at least partially—a reversible process. It would have been expected that Skp-SlyD-SlyD, after thermally induced unfolding and dissociation into the monomeric subunits, would aggregate very quickly and quantitatively at an elevated temperature such as 60° C. Yet, we find that Skp-SlyD-SlyD is able to readopt its native-like conformation when the protein solution is chilled to 20° C. Indeed, the near UV CD spectra monitored prior to and after the thermally induced unfolding, virtually superimpose (see FIG. 9). In conclusion, Skp-SlyD-SlyD possesses robust folding properties which are outstanding for a molecule of this complexity and which are highly desired for a molecule that serves as an anti-interference or generally stabilizing component of an immunoassay.

Figure 11:
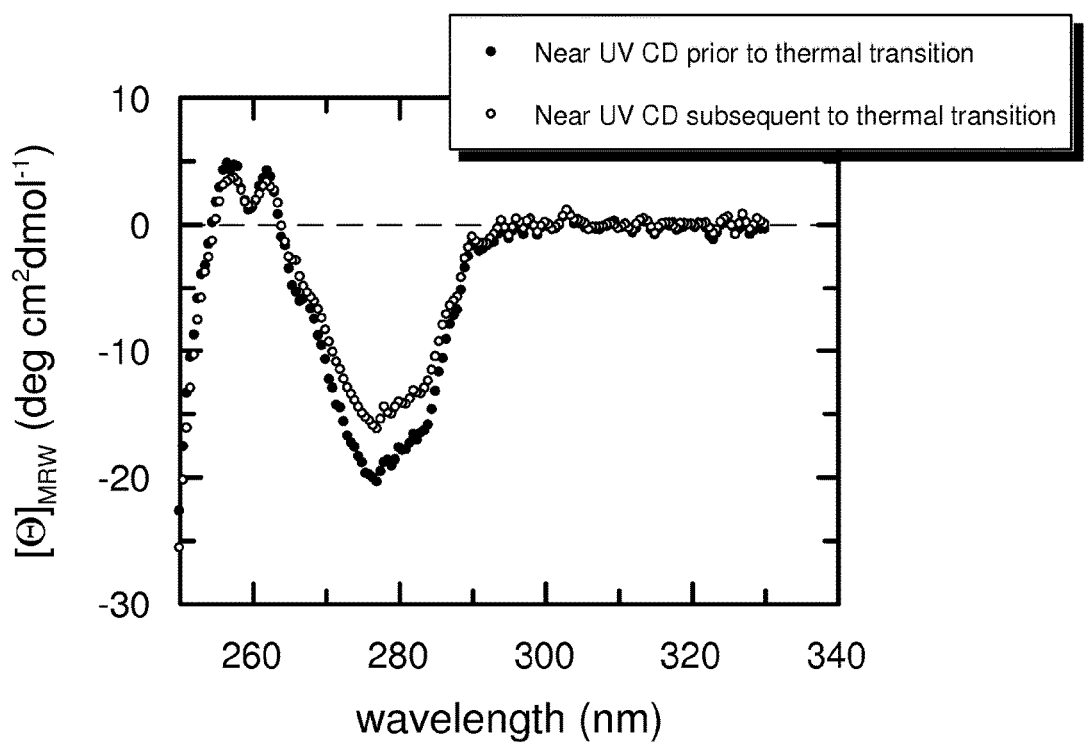
FIG. 11 shows near-UV CD spectra of Skp-SlpA-SlpA in the range of 250-330 nm (see example 5).

We found very similar results for Skp-SlpA-SlpA: just like Skp-SlyD-SlyD, Skp-SlpA-SlpA exhibits a marked CD signal in the near UV region (250-330 nm, signal maximum at 277 nm), pointing to a well-ordered conformation after the matrix-coupled refolding process. By means of thermal transitions (monitored at 277 nm) we observed that Skp-SlpA-SlpA retains its native-like conformation at temperatures up to 55° C. Furthermore, the CD signal of the native molecule is largely restored after a thermal unfolding/refolding cycle (20° C./65° C./20° C.) as illustrated by FIG. 11. It is desirable that anti-interference additives exert their functions even under temperature conditions that are far from optimal. The high thermal stability of Skp-SlpA-SlpA together with the partial reversibility of its thermally-induced unfolding underscores the robustness of this molecule.

In conclusion, Skp-SlyD-SlyD and Skp-SlpA-SlpA possess robust folding properties which are outstanding for molecules with this degree of complexity and which are highly desirable for modules that serve as anti-interference or generally stabilizing components of an immunoassay.

The invention claimed is:

1. A fusion polypeptide comprising one multimerization domain of a chaperone, wherein the chaperone is Skp and at least one molecule selected from the group consisting of SlyD and SlpA.

2. The fusion polypeptide according to claim 1, wherein Skp is fused to two adjacent molecules of SlyD or SlpA.

3. A fusion polypeptide comprising SEQ ID NO. 1 (Skp-tandem-SlyD).

4. A fusion polypeptide comprising SEQ ID NO. 9 (Skp-tandem-SlpA).

5. The fusion polypeptide according to claim 1, further comprising a glycine rich spacer.

6. The fusion polypeptide according to claim 1, further comprising a histidine tag.

* * * * *